(12) United States Patent
Schmälzle

(10) Patent No.: US 11,284,967 B2
(45) Date of Patent: Mar. 29, 2022

(54) BONE FOUNDATION GUIDE SYSTEM WITH REDUCTION GUIDE

(71) Applicant: Swissmeda AG, Baar (CH)

(72) Inventor: Stefan Schmälzle, Rifferswil (CH)

(*) Notice: Subject to any disclaimer, the term of this patent is extended or adjusted under 35 U.S.C. 154(b) by 350 days.

(21) Appl. No.: 16/183,986

(22) Filed: Nov. 8, 2018

(65) Prior Publication Data

US 2020/0146770 A1 May 14, 2020

(51) Int. Cl.
| | | |
|---|---|---|
| G06T 15/00 | (2011.01) | |
| A61C 1/08 | (2006.01) | |
| A61C 8/00 | (2006.01) | |
| A61C 9/00 | (2006.01) | |
| A61C 13/00 | (2006.01) | |
| A61C 13/34 | (2006.01) | |
| G06T 7/60 | (2017.01) | |
| B33Y 50/00 | (2015.01) | |
| A61B 34/10 | (2016.01) | |

(52) U.S. Cl.
CPC ............ *A61C 1/084* (2013.01); *A61C 8/0089* (2013.01); *A61C 9/004* (2013.01); *A61C 13/0004* (2013.01); *A61C 13/34* (2013.01); *B33Y 50/00* (2014.12); *G06T 7/60* (2013.01); *A61B 2034/104* (2016.02); *A61C 8/0095* (2013.01)

(58) Field of Classification Search
CPC ......... G06T 7/60; A61C 8/0095; A61C 9/004; A61C 1/084; A61C 13/0004; A61C 8/0089; A61C 2034/104; A61C 13/34; B33Y 50/00
USPC ......................................................... 345/418
See application file for complete search history.

(56) References Cited

U.S. PATENT DOCUMENTS

| | | | |
|---|---|---|---|
| 8,956,158 B2* | 2/2015 | Schmalzle | A61C 1/082 433/76 |
| 9,283,055 B2* | 3/2016 | Thompson, Jr | A61C 8/0089 |
| 10,307,226 B2* | 6/2019 | Llop | A61C 1/084 |
| 10,639,129 B2* | 5/2020 | Llop | A61C 13/0004 |
| 2013/0071811 A1 | 3/2013 | Groscurth et al. | |

FOREIGN PATENT DOCUMENTS

| | | |
|---|---|---|
| EP | 2797547 B1 | 11/2014 |
| WO | 2017069789 A1 | 4/2017 |

OTHER PUBLICATIONS

Van Assche N, Vercruyssen M, Coucke W, Teughels W, Jacobs R, Quirynen M. Accuracy of computer-aided implant placement. Clinical oral implants research. Oct. 2012;23:112-23.*

* cited by examiner

*Primary Examiner* — Phu K Nguyen

(57) ABSTRACT

A bone foundation guide system for a dental implant surgical site has a bone foundation guide and a dental implant surgical guide with an open surgical space therebetween. The top of the foundation guide body is contoured and has an upper surface to attach a bottom surface of the dental implant surgical guide as well as to define a removal and augmentation level and to guide the removal and/or augmentation of bone segments from the dental surgical site via a separation plane. The separation plane has a central area predetermined to define an implant depth of bores for anchoring implants, and further has an inclined area extending from all side ends of the central area towards the first bridge end and the second bridge end raising above the removal and augmentation level of the jaw bone.

3 Claims, 7 Drawing Sheets

BONE FOUNDATION GUIDE SYSTEM WITH REDUCTION GUIDE

BACKGROUND OF THE INVENTION

Field of the Invention

The present invention relates to a bone foundation guide system for a dental implant surgical site comprising bone foundation guide and a dental implant surgical guide, wherein the bone foundation guide comprises a foundation guide body having a foundation guide buccal wall and a foundation guide lingual wall that are continuously connected by a first bridge end and a second bridge end forming an open surgical space connecting a top of the foundation guide body with a bottom of the foundation guide body, wherein the foundation guide buccal wall and the foundation guide lingual wall comprise abutment portions to reversibly affix the foundation guide body to at least a portion of a bone segment at the dental implant surgical site, wherein the top of the foundation guide body is contoured and comprises an upper surface to attach a bottom surface of the dental implant surgical guide as well as to define a removal and augmentation level and to guide the removal or augmentation or both of bone segments from the dental surgical site.

Description of Related Art

WO 2017/069789 discloses such a bone foundation guide system providing a solid anchorage for the dental restorative process. It starts from the knowledge of someone skilled in the art that, initially, the remaining teeth are to be extracted and then the exposed bone has to be properly prepared, especially reduced or augmented, with help of a bone foundation guide. Then a dental implant surgical guide is subsequently fitted and attached at the place of the remodelled bone of the dental surgical site. Previously the bone foundation guide and the implant dental surgical guide for the implants were considered to be separate instruments. WO 2017/069789 suggests providing bone foundation guide comprising a body having a buccal wall and lingual wall that is continuously connected by a first end and a second end forming an open surgical space connecting a top of a body with the bottom of the body. The bottom is contoured to reversibly affix a body to at least a portion of a bone segment at the dental implant surgical site while the top is contoured to attach a bottom side of a dental implant surgical guide as well as to guide the removal or augmentation or both of the bone segments from a dental surgical site. US 2013/0071811 A1 discloses a dental surgical drill guide assembly comprising an edentulous surgical guide intended to fit both gum tissue and a number of small areas of jaw bone.

SUMMARY OF THE INVENTION

The invention is based on the insight that a bone foundation guide system for a dental implant surgical site comprising bone foundation guide and a complementary dental implant surgical guide is the basis for a fast achievement of the necessary bone level for an implant but that the production process of the two complementary templates should be easier and faster with a high degree of security when the implant sites for the denture are determined by the dental surgeon.

A bone foundation guide comprises a foundation guide body having a foundation guide buccal wall and a foundation guide lingual wall that are continuously connected by a first bridge end and a second bridge end forming an open surgical space connecting a top of the foundation guide body with a bottom of the foundation guide body, wherein the foundation guide buccal wall and the foundation guide lingual wall comprise abutment portions to reversibly affix the foundation guide body to at least a portion of a bone segment at the dental implant surgical site. Said foundation guide body and the abutment portions can especially be produced according to EP 2 797 547 A1 of the applicant. The top of the foundation guide body is contoured and comprises an upper surface to attach a bottom surface of the dental implant surgical guide as well as to define a removal and augmentation level and to guide the removal or augmentation or both of bone segments from the dental surgical site. In other words, the level of this separation plane defines the level of reduction of existing bone material. But since this plane is between the two elements, i.e. the bone foundation guide and the complementary dental implant surgical guide of the system, it is important to allow a correct and quick determination of this plane. Therefore, the separation plane between the upper surface of the foundation guide body and the lower surface of the dental implant surgical guide comprises a central area predetermined based on a predetermined implant depth based on bores for anchoring implants, and further comprises an inclined area extending from all side ends of the central area towards the first bridge end and the second bridge end raising above the removal and augmentation level of the jaw bone. It is therefore quite easy for the surgeon to define the parameters of the plane separating the two guides, choosing an offset over the predetermined implant depth, wherein the central area covers from side to side the outermost implant sites.

Preferably, the two guides are fully complementary, i.e. the dental implant surgical guide comprises a surgical guide body having a surgical guide buccal wall and a surgical guide lingual wall which are provided to be on top of the respective buccal wall and lingual wall of the bone foundation guide, and that these walls are continuously connected by a third bridge end and a fourth bridge end which are centered on the first and second bridge end of the bone foundation guide. Thus, the surgical guide also contours said open surgical space connecting the top of the surgical guide body with the bottom of the surgical guide body, wherein the separation plane is provided between the respective buccal walls, the respective lingual walls as well as between the respective bridge ends.

The separation plane between the upper surface of the foundation guide body and the lower surface of the dental implant surgical guide comprise said central area predetermined to define an implant depth of bores for anchoring implants. Usually, if there are only two bores the central area is defined between those. If there would be four implant places, two inner and two outer implants, then the central area would be extended between the outer implant places. The area can be flat, e.g. especially oriented horizontal as the lower jaw of a patient but can comprise curvatures to allow reduced bone materials, where augmentation is not possible or planned. The separation plane further comprises an inclined area extending from all side ends of the central area towards the first bridge end and the second bridge end raising above the removal and augmentation level of the jaw bone.

The plane of the central area is preferably chosen to be normal to the axis of each of said bores for anchoring implants and is distant to the predetermined implant depth by a predetermined offset. Therefore the central area is usually not entirely flat but comprises spline-calculated flat segments being normal to the axis of the bores of the implant sites and interconnecting and continuously connecting plane portions.

The separation plane can further comprise adjacent to the inclination plane areas transitional bridging portions with a greater inclination than the inclination plane areas for centring the position of the side ends of the dental implant surgical guide on the first and second bridge ends. Then a first inclination is followed by a steeper second inclination allowing an easier positioning of the drill surgical guide on the bone foundation guide.

The first and second bridge ends of the lower guide may have bridge abutment portions on the underside to have further abutment points beside abutment points on the bone foundation guide.

The upper surface of the foundation guide body and the lower surface of the dental implant surgical guide are preferably complementary one to the other so that the outer and inner walls of the foundation guide body and the dental implant surgical guide are flush one to the other and therefore define the same width of the separation plane extending from the exterior buccal wall to the exterior lingual wall along and outside the jawbone.

Said width of the separation plane which is changing from end to end of the system is predetermined based on the transverse width of the bone, adjacent gum on both sides of the bone and the width of the buccal wall and exterior lingual wall of the system to avoid undercuts of the guide system.

A computer implemented method for producing a bone foundation guide system comprises the steps of gathering data of a three-dimensional model of the jaw bone and the oral cavity of a patient and storing said data in a computer memory, defining position and orientation of at least two drill bore positions in the three-dimensional model data and storing said data in a computer memory, defining a separation plane between the bone foundation guide and a dental implant surgical guide as three-dimensional model data comprising a central area and connecting inclination areas at the sides towards the bridge ends, wherein the central area plane is defined as jaw bone level to be reached through reduction or augmentation based on a parameter of implant depth of the drill bore positions; wherein the inclination plane area connecting at the central area plane is defined on a length of the inclination plane area and a height over the implant depth and/or over the level of the central area and storing said data in a computer memory; and transforming the stored data into signal data for a production machine, as a rapid-prototyping apparatus or a milling apparatus.

The separation plane comprising the central area and the inclination plane area is preferably determined following a spline based calculation.

In other words, the planned final implant positions are used to construct the reduction surface of the construction. The reduction surface is used to define the desired bone level of the process and is used to partition the template into a bone foundation or reduction template and an implant guide template. The reduction surface is derived from the implant positions and predetermined floating point numbers describing the shape of the reduction surface. First there is an offset parameter with describes the distance of the reduction surface to the bone level of the implants, i.e. a height parameter. Furthermore there are pairs of values describing the shape of the reduction surface in the region from the most distal implants 'out of the bone'.

The width of the reduction surface is adjusted to fit the requirement of the reduction surface to be used as bone reduction and template partitioning surface. The surface of the bone foundation guide is also computed in such a way that there are no backcuts in the direction of insertion of the template by filtering out the portions of the boundary curves of the reduction surface which would otherwise constitute backcuts in the direction of insertion of the template.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF THE INVENTION

Figure 1:
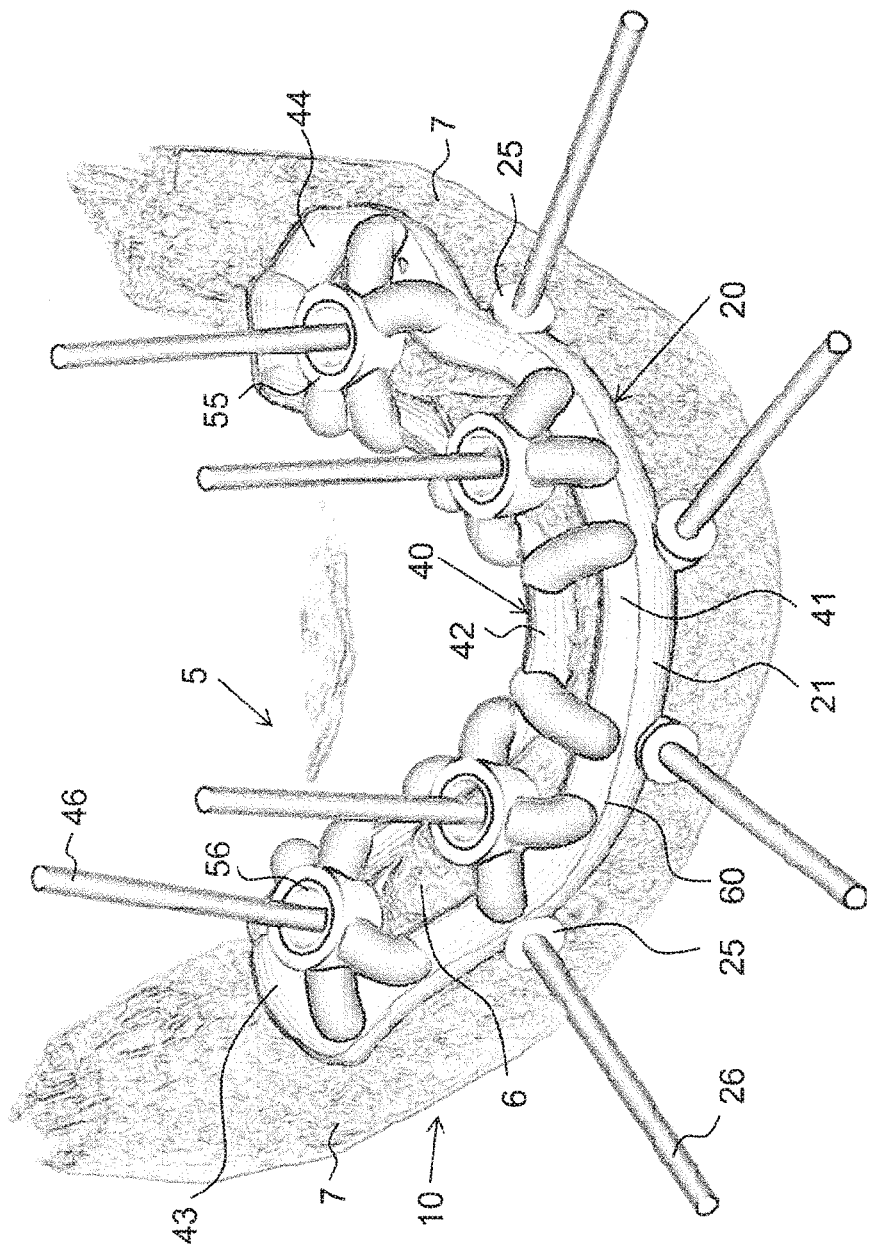
FIG. 1 shows a schematical perspective view of a dental surgical site with a bone foundation guide system according to an embodiment of the invention fixed thereon.
Figure 2:
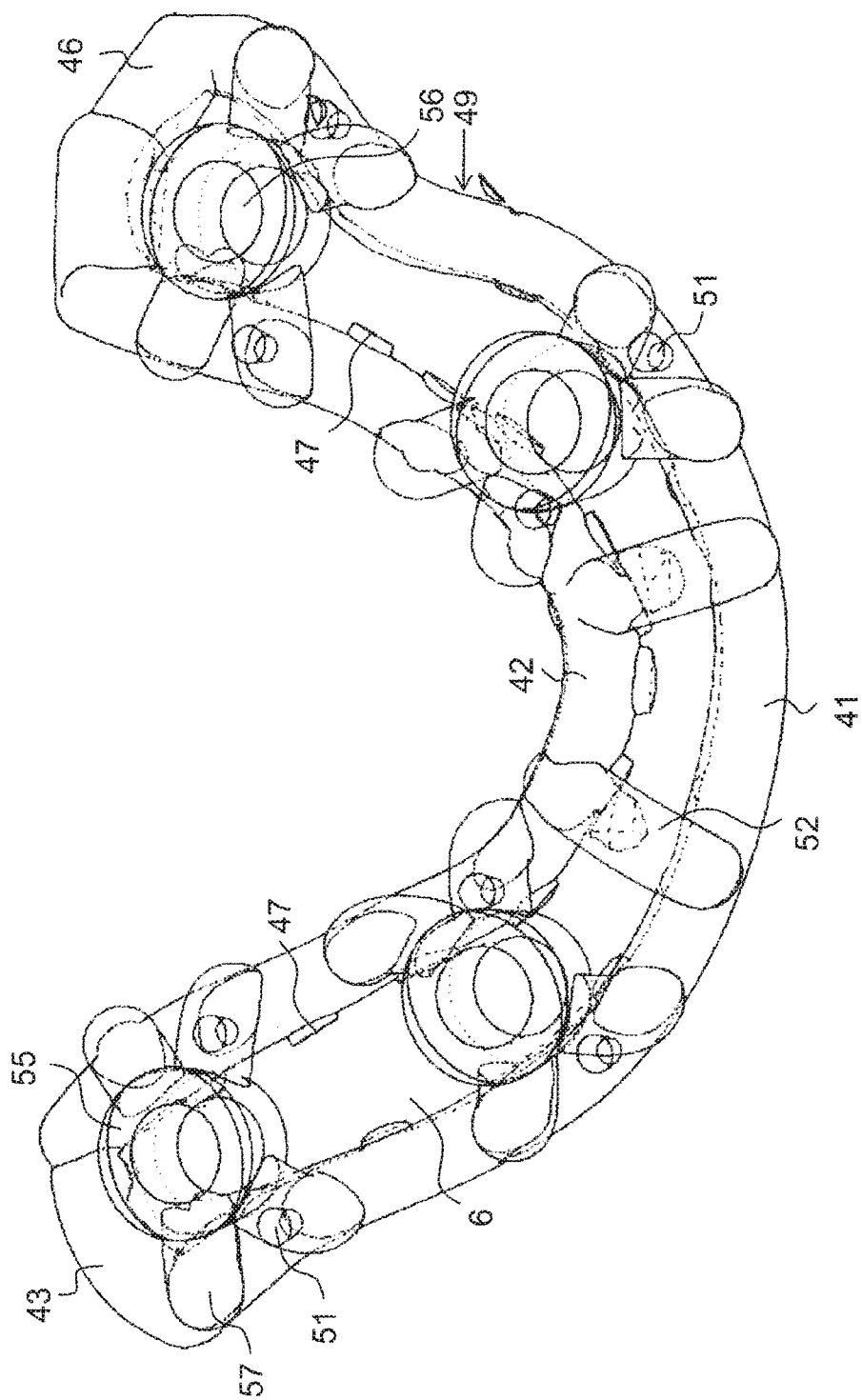
FIG. 2 shows a schematical perspective view of the dental implant surgical guide of FIG. 1.
Figure 3:
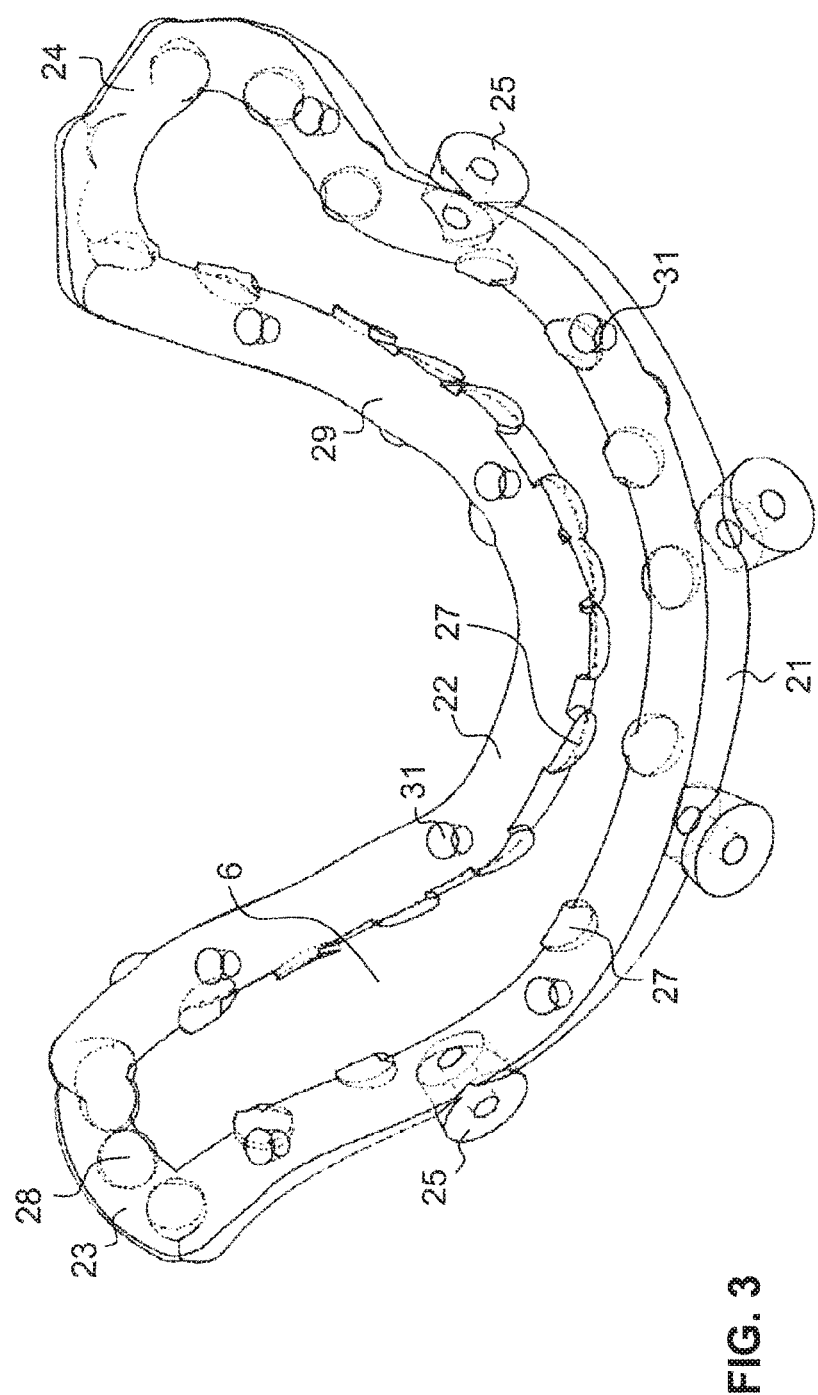
FIG. 3 shows a schematical perspective view of the bone foundation guide of FIG. 1.

FIG. 1 shows a schematical perspective view of a dental surgical site 5 with a bone foundation guide system 10 according to an embodiment of the invention fixed thereon. The dental surgical site 5 shown in FIG. 1 is the lower jaw. FIG. 2 shows a schematical perspective view of the dental implant surgical guide 40 of FIG. 1 and FIG. 3 shows a schematical perspective view of the bone foundation guide 20 of FIG. 1.

The bone foundation guide system 10 comprises a lower bone foundation guide 20 and an upper dental implant surgical guide 40. The two guides 20 and 40 have a common surface and are separated by this surface which is called separation plane 60 shown as a line between the two mentioned guides 20 and 40. The bone foundation guide 20 is fixed on the jaw bone 7 of the patient with guide body fasteners 26 which are positioned through attachment apertures 25 in the bone foundation guide 20 material. The attachment apertures 25 are provided here at four different places at the buccal wall 21 of the bone foundation guide 20. The bone foundation guide 20 as shown in FIG. 3 comprises a buccal wall 21, a lingual wall 22 connected at both ends via ridge portions 23 and 24. Abutment portion 27 are distributed in a predetermined way as e.g. shown in EP 2 797 547 A1 along the inner walls of the buccal wall 21 as well as the lingual wall 22 as contact points with the dental surgical side 10 and there either with the jaw bone 7 or gum covered areas. The two sides of abutment portion 27 are enclosing the surgical space 6. As it can be seen from FIG.

3 the upper surface of the bone foundation guide 20 has received the reference numeral 29 and continues as an essentially horizontal plane with almost no inclination in the longitudinal direction of the slightly curved surgical space 6, following the curvature of the jaw, across a diameter of the buccal 21 or lingual 22 wall at the place where the incisors and the corner teeth are used to be. The horizontal plane can be slightly inclined from the buccal side surface to the lingual side surface, if one of the two walls 21 and 22 would be provided higher than the other one. As it can be seen in the FIGS. 1 to 3 there is a clear inclination change towards the free end bridges 23 and 24 which will be explained later on in the specification. The bridges 23 and 24 are contacting the environment of the surgical site 6 with abutment portions 28. A number of positioning holes 31 are provided in the body of the bone foundation guide 20. These holes 31 are intended to be complementary to similar elements 51 in the surgical drill guide 40.

The dental implant surgical guide 40 as shown in FIG. 2 has a similar buccal wall 41 and lingual wall 42 as the bone foundation guide 20 positioned below it and the lower surface 49 under the walls 41 and 42 is complementary to the upper surface 29 of the bone foundation guide 20. Abutment portions 47 are provided on the inside of the walls 41 and 42 to position the foundation guide 40 on the surgical site 6 as well. The buccal wall 41 and the lingual wall 42 are separated by an open surgical space 6 which is the same space as for the bone foundation guide 20. Here, webs 52 are provided for contacting the buccal wall 41 with the lingual wall 42 to strengthen the structure. Drill guides 55, e.g. hollow sleeves, are provided with inner trough going holes 56 directed through the surgical space 6 towards the jaw bone 7, here positioned at four different places with four positioning webs 57 each which are attached at the relevant portions of the buccal wall 41 or lingual wall 42 along the surgical space 6 between the bridges 23, 43 and 24, 44.

Pins 51 are provided on the underside of the dental implant surgical guide 40 at the positions complementary to the positioning holes 31 in the bone foundation guide 20 to combine the two guides 20 and 40 into the device 10 as shown in FIG. 1. The implant rods 46 are shown to be positioned in the holes 56 of the drill guides 55.

Figure 4:
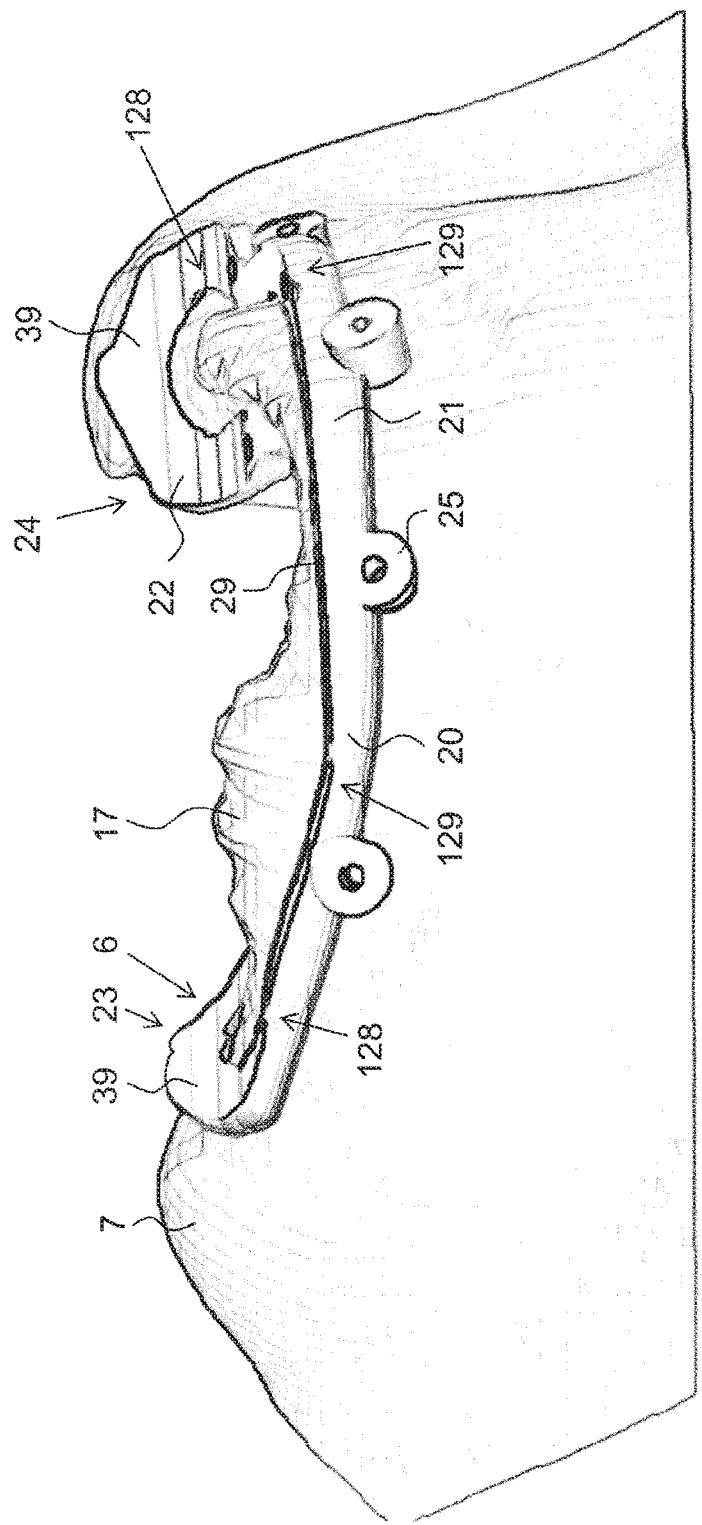
FIG. 4 shows a side view of the dental surgical site of FIG. 2 with the bone foundation guide of FIG. 3 before reduction of the bone segment at the dental surgical site.

FIG. 4 shows a side view of the dental surgical guide 40 of FIG. 2 with the bone foundation guide 20 of FIG. 3 before reduction of the bone segment 17 at the dental surgical site 6. It can well be seen that the upper surface 29 of the buccal wall 21 is essentially horizontal and flat and has a kink 129 with a rising inclination towards the upper end bridge surface 39 of bridge 23. The turning point 128 of the end of buccal wall 21 to the bridge 23 portion is inclined with a steeper angle compared to the horizontal central portion of the surface 29. The surgical space 6 between the buccal wall 21 and the lingual wall 22, which is in FIG. 4 in the background, is already edentulous but still filled with bone material to be removed 17. In this respect the surfaces 29 on both walls 21 and 22 are referencing the height of the material to be removed, or the material to be augmented if portions of the bone would be missing, i.e. having a level being lower than the level defined by the surfaces 29 of the walls 21 and 22 and the virtual plane between them.

Figure 5:
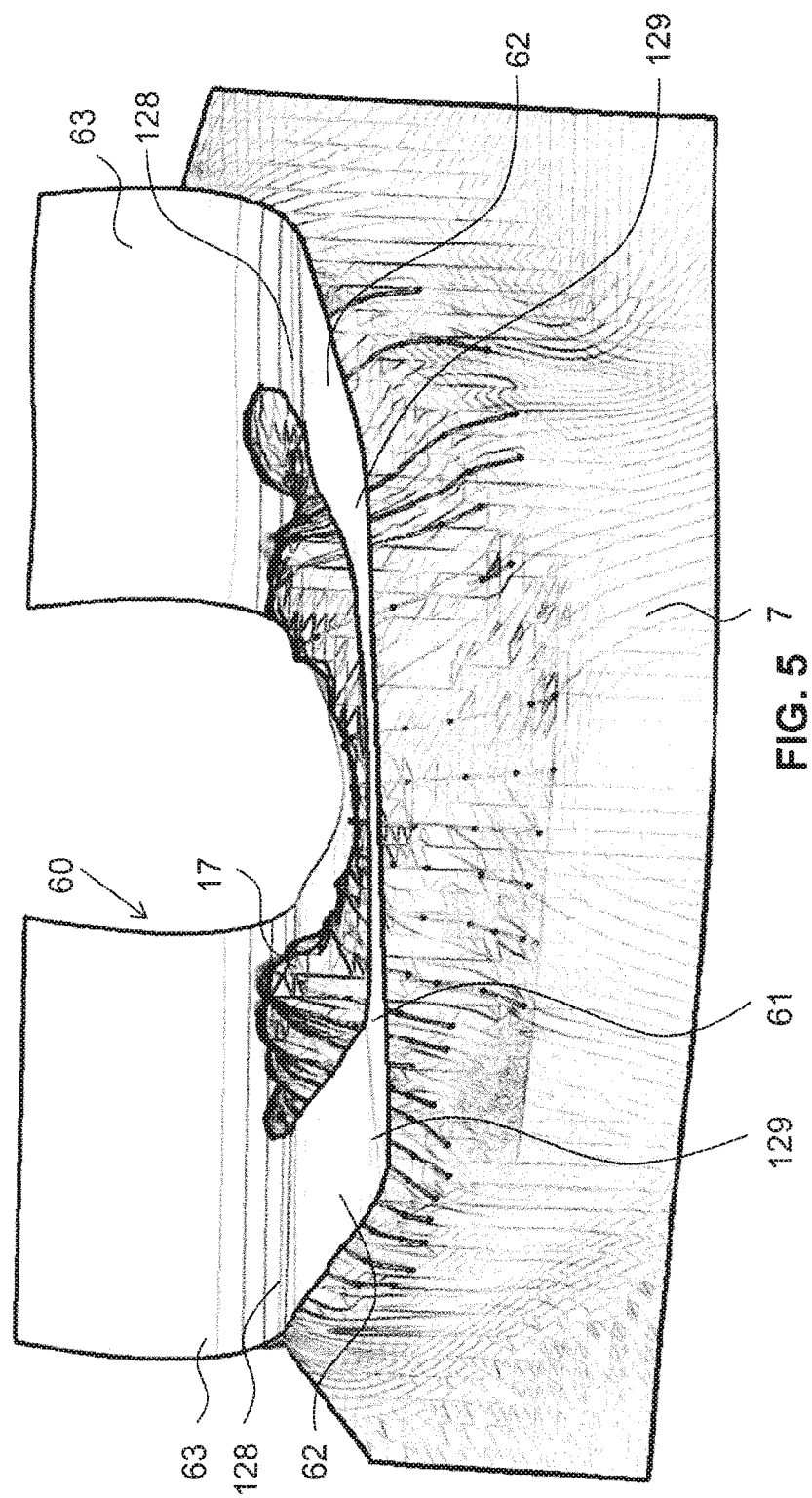
FIG. 5 shows a perspective view of the dental surgical site of FIG. 4 with the separation plane between the bone foundation guide and the dental implant surgical guide according to an embodiment of the invention.
Figure 6:
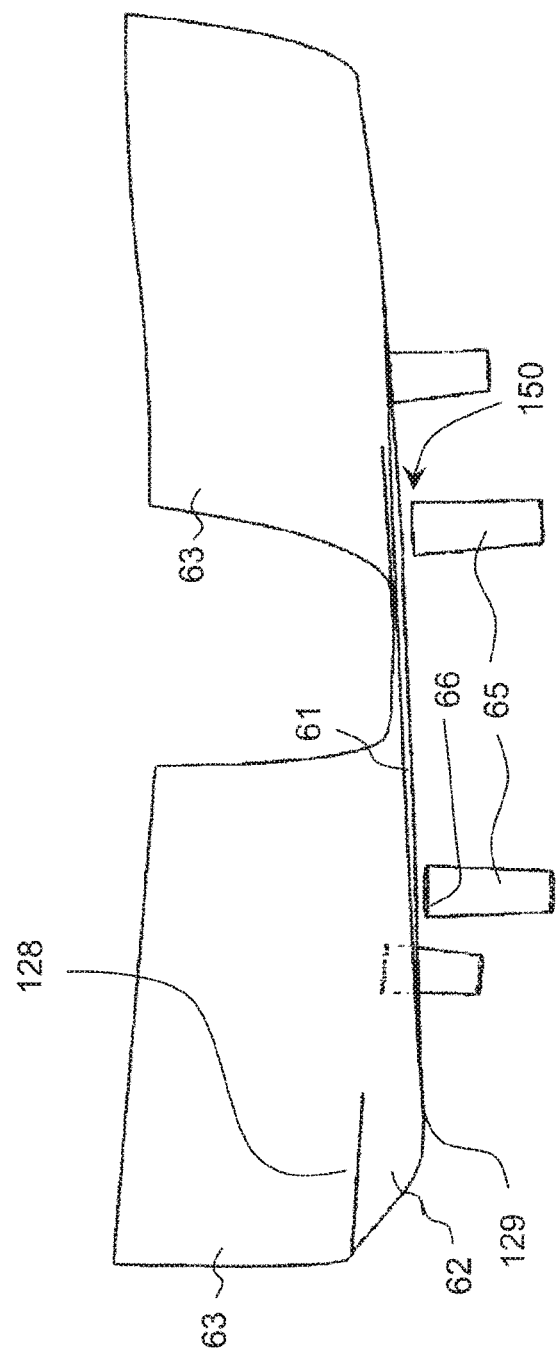
FIG. 6 shows a perspective view of the separation plane of FIG. 5 with four plane orientation defining drill positions.

FIG. 5 shows a perspective view of the dental surgical site 6 of FIG. 4 with the separation plane 60 between the bone foundation guide 20 and the dental implant surgical guide 40 according to an embodiment of the invention and FIG. 6 shows a perspective view of the separation plane 60 of FIG. 5 with four plane orientation defining drill positions 65. The separation plane 60 shown in FIG. 5 and FIG. 6 is the plane at or between the upper surface 29 of the bone foundation guide 20 and the lower surface 49 of the dental implant surgical guide 40. This surface 60 has a central portion 61 mainly in front and behind of the front teeth or the future front replacement teeth of the patient with an essential horizontal level, e.g. between the corner teeth and the first molars, if applicable. Then, an intermediate space plane 62 after the kink 129 continuously provides the surgical space for the bone material removal 17 for the further teeth having already a slight increase of the inclination. Then there is a transitional portion 63 behind the turning line 128 at or slightly before the zone where the walls 21, 22, 41, 42 are joined together with bridge portions 23, 24, 43, 44, wherein the transition consists of the fact that the surface 60 leaves the room below the level of the bone to be maintained and the untouched jaw bone 7 in the back of the mouth of the patient. In other words, the surface 39 of the upper end bridge surface of the bone foundation guide 20 is inclined in view of the surgical space to be able raising out of the bone material so that the bridge portion 23, 24 with the contact abutment points 28 is positioned on untouched and unmachined jaw bone material.

The invention provides a parameter allowing to calculate the inclination from the central portion surface 61 towards the transitional portion 63 in order to be able to cut the bone material essentially horizontally in the middle area and to leave the jaw bone towards the bridge portions. For that and as shown in FIG. 6, the defined drill positions 65 of the outer most later implant rods 46 are taken as reference, because these outer most implant abutments have to be anchored in the bone itself at a predetermined implant depth 150 so that the change of inclination for the plane 60 to leave the bone material can only start outside of these areas towards the bridge portions. The implant depth 150 is predetermined by the surgeon as a distance between the top surface 66 screw position shown as defined drill position 65 in FIG. 6 and the separation plane 60, here at the end of surface 61 at kink 129.

As explained above, the present invention uses a combined bone foundation guide system 10 for the dental implant surgical site 6 comprising said bone foundation guide 20 and said dental implant surgical guide 40 connected at the common separation plane 60 which serves at the same time as level providing guide for removing or augmenting bone material 17 at the surgical site 6 in between. Both the bone foundation guide 20 as well as said dental implant surgical guide 40 can be produced with the method disclosed in and according to EP 2 797 547 A1 using e.g. spline functions to contour the guides according to the anatomy of the patient. The separation plane 60 can be defined in such a method to produce the two parts 20 and 40 of the bone foundation guide system with a reduced number of parameters as follows.

Figure 7:
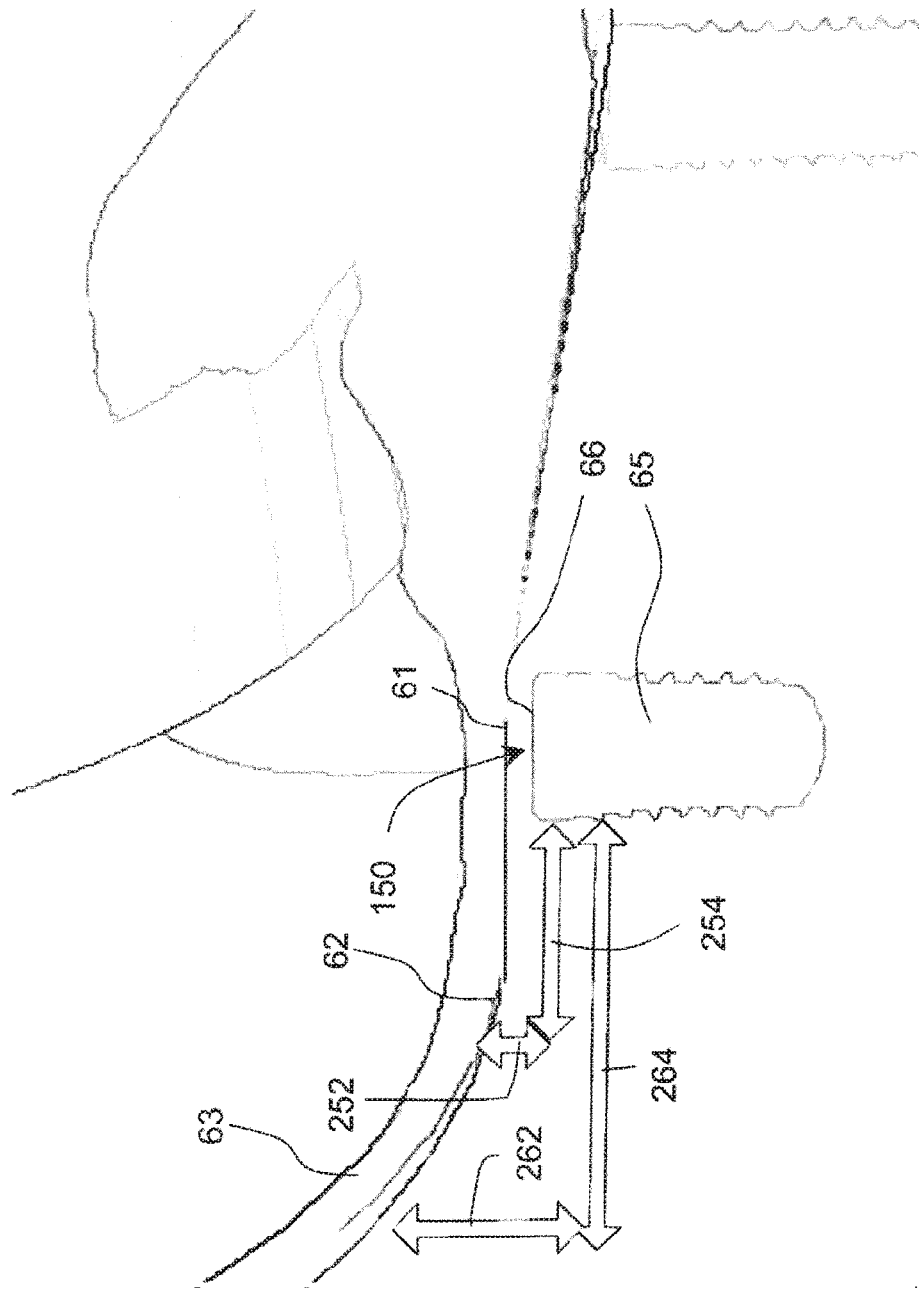
FIG. 7 shows a perspective view of the dental surgical site of FIG. 5 and the separation plane and drill bores of FIG. 6 with parameters to define the position and contour of said separation plane in the bone foundation guide system elements.

FIG. 7 shows a perspective view of the dental surgical site 6 of FIG. 5 and the separation plane 60 and drill bores 65 of FIG. 6 with parameters to define the position and contour of said separation plane 60 in the bone foundation guide system elements 20 and 40. In order to readily produce the separated bone foundation guide 20 and dental implant surgical guide 40 with a matching separation plane, it is sufficient according to an embodiment of the invention to define the intended distance and depth 150 between the upper surface 66 of the drill bore 65 and thus the position of the implant as well as the necessary slope of the separation plane 60 to leave the bone level to be machined or to be augmented at the site 61. Therefore double arrow 252 shows the height difference to be reached over the distance 254 providing the slope of portion 62 as well as the double arrow 262 showing the height difference to be reached over the distance 264 towards the bridge ends 23 and 24, where abutment portions 28 are intended to affix the bone foundation guide 20 at the side ends of the surgical site 6.

The invention claimed is:

1. A computer-implemented method for producing a bone foundation guide system, the method comprising the steps of:
    gathering data of a three-dimensional model of the jaw bone and the oral cavity of a patient and storing said data in a computer memory;
    defining position and orientation of at least two drill bore positions in the three-dimensional model data and storing said data in the computer memory;
    defining a three-dimensional model of the bone foundation guide system comprising a bone foundation guide and a dental implant surgical guide, wherein the model of the bone foundation guide comprises a foundation guide body having a foundation guide buccal wall and a foundation guide lingual wall that are continuously connected by a first bridge end and a second bridge end forming an open surgical space connecting a top of the foundation guide body with a bottom of the foundation guide body, wherein the foundation guide buccal wall and the foundation guide lingual wall comprise abutment portions to reversibly affix the foundation guide body to at least a portion of a bone segment at the dental implant surgical site, wherein the top of the foundation guide body is contoured and comprises an upper surface to attach a bottom surface of the dental implant surgical guide as well as to define a removal and augmentation level and to guide the removal or augmentation or both of bone segments from the dental surgical site;
    defining a separation plane between the bone foundation guide and the dental implant surgical guide as three-dimensional model data comprising a central area and connecting inclination areas at the sides towards the bridge ends, wherein the central area plane is defined as jaw bone level to be reached through reduction or augmentation based on a parameter based on implant depth of predetermined drill bore positions, wherein the inclination plane area connecting at the central area plane is defined on a length of the inclination plane area and a height over the implant depth or over the level of the central area and is extending from all side ends of the central area towards the first bridge end and the second bridge end raising above the removal and augmentation level of the jaw bone and storing said data in a computer memory; and
    transforming the stored data into signal data for a production machine chosen from the group encompassing a rapid-prototyping apparatus or a milling apparatus, for the production of the bone foundation guide system.

2. The method according to claim 1, wherein the separation plane comprising the central area and the inclination plane area is determined following a spline based calculation.

3. The method according to claim 1, wherein the foundation guide buccal wall and the foundation guide lingual wall of the bone foundation guide is predetermined so that there are no backcuts in the direction of insertion of the bone foundation guide by filtering out the portions of the boundary curves of the reduction surface which would otherwise constitute undercuts in the direction of insertion of the bone foundation guide.

* * * * *